(12) United States Patent
Beria et al.

(10) Patent No.: US 6,838,547 B2
(45) Date of Patent: Jan. 4, 2005

US006838547B2

(54) GLUTATHIAONE CONJUGATES WITH DISTAMYCIN DERIVATIVES HAVING ANTITUMORAL ACTIVITY

(75) Inventors: Italo Beria, Nerviano (IT); Paolo Cozzi, Milan (IT); Maria Cristina Geroni, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 10/380,375

(22) PCT Filed: Sep. 7, 2001

(86) PCT No.: PCT/EP01/10397

§ 371 (c)(1),
(2), (4) Date: Aug. 12, 2003

(87) PCT Pub. No.: WO02/22655

PCT Pub. Date: Mar. 21, 2002

(65) Prior Publication Data

US 2004/0038905 A1 Feb. 26, 2004

(30) Foreign Application Priority Data

Sep. 15, 2000 (IT) ..................................... MI2000A2012

(51) Int. Cl.⁷ .......................... A61K 38/04; A61K 38/00
(52) U.S. Cl. .......................... 530/329; 530/330; 514/16; 514/17
(58) Field of Search ..................... 514/16, 17; 530/329, 530/330

(56) References Cited

U.S. PATENT DOCUMENTS 5,158,856 A  * 10/1992 Usagawa et al. ........... 430/264
5,646,177 A    7/1997 Koch et al.
5,880,097 A    3/1999 Lyttle et al.

FOREIGN PATENT DOCUMENTS

| EP | 0 265 719 A   |   | 5/1988  |
|----|---------------|---|---------|
| EP | 0 420 121 A   |   | 4/1991  |
| EP | 0543576       | * | 5/1993  |
| WO | 98 21202 A    |   | 5/1998  |
| WO | 99 50265 A    |   | 10/1999 |
| WO | 00 06541 A    |   | 2/2000  |
| WO | 01 851 44 A   |   | 11/2001 |

OTHER PUBLICATIONS

Burchenal, et al, Cancer, the Outlaw Cell, Second Edition, Richard Lafond, Ed. American Chemical Society Books, 1988. pp. 204–205.*

Beria et al. J. Med. Chem. 2004. vol. 47, pp. 2611–2623.*

* cited by examiner

Primary Examiner—Christopher R. Tate
Assistant Examiner—Edward Ward
(74) Attorney, Agent, or Firm—Scully, Scott, Murphy & Presser

(57) ABSTRACT

The present invention refers to distamycin and derivatives thereof, such as bromo- or chloro-acryloyl derivatives of distamycin, which are conjugated with glutathione, to a process for their preparation and to pharmaceutical compositions thereof. The compounds of the invention are endowed with a remarkable antitumor activity and are thus useful in therapy in the treatment of cancer.

13 Claims, No Drawings

GLUTATHIAONE CONJUGATES WITH DISTAMYCIN DERIVATIVES HAVING ANTITUMORAL ACTIVITY

The present invention refers to distamycin derivatives having antitumoral activity and, more in particular, it refers to acryloyl derivatives of distamycin conjugated with glutathione, their preparation process and the pharmaceutical compositions thereof.

Distamycin A is an antibiotic substance having antiviral and oncolytic properties characterized by a polypyrrole structure. [*Nature* 203; 1064 (1964); *J Med. Chem.* 32: 774–778 (1989)].

The international patent applications WO 90/11277, WO 98/04524, WO 98/21202, WO 99/50265, WO 99/50266 and WO 01/40181 (claiming priority from British patent application No. 9928703.9), all in the name of the Applicant itself and herewith incorporated as a reference, describe acryloyl derivatives of distamycin in which the amidine end moiety is optionally substituted by nitrogen groups such as, for instance, cyanamidine, N-methylamidine, ethylguanidine, amide, amidoxirne, cyano groups or analogues thereof, and/or where the polypyrrole structure of distamycin, or parts of it, are substituted by different carbocyclic or heterocyclic structures.

Now we have unexpectedly found that the above reported acryloyl derivatives of distamycin, properly conjugated with glutathione, result to be endowed with a remarkable antitumoral activity.

It is therefore an object of the present invention a distamycin derivative of formula (I)

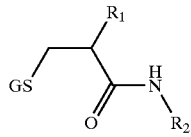

(I)

wherein:
$R_1$ is a bromine or chlorine atom;
$R_2$ is a distamycin or a distamycin-like structure;
GS represents a radical of formula (II)

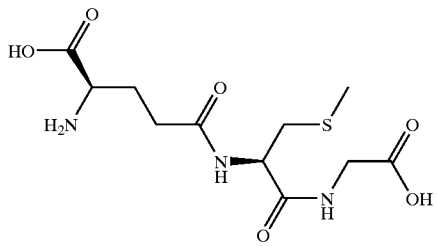

(II)

consisting of glutathione bound to the rest of the molecule through the sulfur atom; or a pharmaceutically acceptable salt thereof.

The present invention includes, in its scope, all the possible isomers of the compounds of formula (I), both considered separately and in admixture, as well as the metabolites and the pharmaceutically acceptable bio-precursors (otherwise known as pro-drugs) of the compounds of formula (I).

In the present description, unless otherwise specified, by the term distamycin or distamycin-like structure $R_2$ it is intended any structure which could be correlated to distamycin itself, for example by substituting the amidine ending moiety and/or the polypyrrole sequence, or parts of it.

Preferred compounds of the invention are the compounds of formula (I) mentioned above, wherein $R_2$ is a group of formula (III):

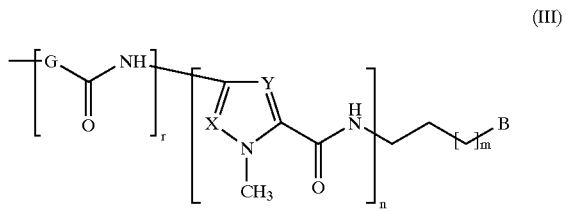

(III)

wherein:
m is 0, 1, or 2; n is an integer number from 2 to 5; r is 0 or 1;
X and Y are, independently for any heterocyclic ring and the same or different from each other, a nitrogen atom or a CH group;
G is phenylene or a saturated or unsaturated penta- or hexa-atomic heterocyclic ring with from 1 to 3 heteroatoms chosen among nitrogen, oxygen or sulfur; or G is a group of formula (IV)

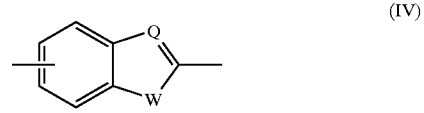

(IV)

wherein Q is a nitrogen atom or a CH group and W is an oxygen or sulfur atom or it is a NR3 group wherein $R_3$ is hydrogen or $C_1$–$C_4$ alkyl;
B is a group chosen among

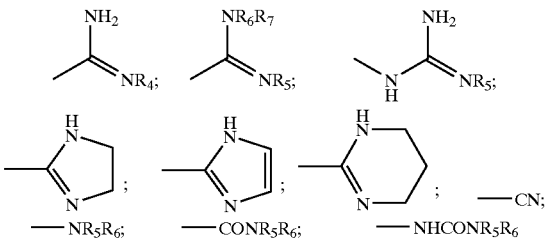

wherein $R_4$ is cyano, amino, hydroxy or $C_1$–$C_4$ alkoxy; $R_5$, $R_6$ and $R_7$, the same or different from each other, are hydrogen or $C_1$–$C_4$ alkyl.

Even more preferred compounds of the invention are the compounds of formula (I) wherein $R_1$ is bromine or chlorine; $R_2$ is a group of formula (III) wherein r is 0, m is 0 or 1, n is 4 and B has the above reported meanings.

Particularly preferred, in this ambit, are the compounds of formula (I) wherein X and Y are both CH groups and B is chosen from:

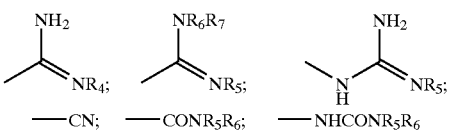

wherein $R_4$ is cyano or hydroxy and $R_5$, $R_6$ and $R_7$, the same or different from each other, are hydrogen or $C_1$–$C_4$ alkyl.

Still more preferred, in this ambit, are the compounds of formula (I) wherein B is chosen between:

wherein $R_5$, $R_6$ and $R_7$ are hydrogen atoms.

In the present description, unless otherwise specified, with the term $C_1$–$C_4$ alkyl or alkoxy it is intended a straight or branched group chosen among methyl, ethyl, n.propyl, isopropyl, n.butyl, isobutyl, sec.butyl, tert. butyl, methoxy, ethoxy, n.propoxy, isopropoxy, n.butoxy, isobutoxy, sec.butoxy or tert.butoxy.

Pharmaceutically acceptable salts of the compounds of formula (I) are the salts with organic or inorganic acids as well as the salts with organic or inorganic bases, pharmaceutically acceptable. For example, pharmaceutically acceptable salts are the salts with hydrochloric, hydrobromic, sulfuric, perchloric, phosphoric, nitric, acetic, trifluoroacetic, propionic, succinic, malonic, tartaric, methanesulphonic or p-toluensulphonic acids, as well as the salts with alkaline or alkalino-earth hydroxides, with carbonates or bicarbonates, or with aliphatic or cycloaliphatic amines, for example methylamine, ethylamine, diethylamine, triethylamine or piperidine.

Specific examples of preferred compounds of formula (I), optionally in the form of pharmaceutically acceptable salts, preferably with hydrochloric acid or with sodium hydroxide, are:

1) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-chloro-3-oxopropyl}sulfanyl)methyl]-2-[(carboxymethyl)amino]-2-oxoethyl}glutamine;

2) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-bromo-3-oxopropyl}sulfanyl)methyl]-2-[(carboxymethyl)amino]-2-oxoethyl}glutamine;

3) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrazol-3-yl)amino]-2-chloro-3-oxopropyl}sulfanyl)methyl]-2-[(carboxymethyl)amino]-2-oxoethyl}glutamine;

4) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrazol-3-yl)amino]-2-bromo-3-oxopropyl}sulfanyl)methyl]-2-[(carboxymethyl)amino]-2-oxoethyl}glutamine;

5) N-5-{1-[({3-[(2-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-imidazol-4-yl)amino]-2-chloro-3oxopropyl}sulfanyl)methyl]-2-[(carboxymethyl)amino]-2-oxoethyl}glutamine;

6) N-5-{1-[({3-[(2-{[(5-{[(5-{[(3-amino-3-aminopropyl)amino]carbonyl}-1-methyl-1H-pyrrol-3-yl)amino]carbonyl}-1-methyl-1H-pyrrol-3-yl)amino]carbonyl}-1-methyl-1H-imidazol-4-yl)amino]-2-bromo-3-oxopropyl}sulfanyl)methyl]-2-[(carboxymethyl)amino]-2-oxoethyl}glutamine;

7) N-5-{1-[({3-[(5-{[(5-{[(5- {[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-bromo-3-oxopropyl}sulfanyl)methyl]-2-[(carboxymethyl)amino]-2-oxoethyl}glutamine;

8) N-5-{1-[({3-[(5-{[(5-{[(5-{[(2-amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-chloro-3-oxopropyl}sulfanyl)methyl]-2-[(carboxymethyl)amino]-2-oxoethyl}glutamine;

9) N-5-{1-[({3-[(5-{[(5-{[(5-{[(2-amino(imino)methyl]amino}ehtyl)amino]carbonyl}-1-methyl-1H-pyrrol-3-yl)amino]carbonyl}-1-methyl-1H-pyrrol-3-yl)amino]carbonyl}-1-methyl-1H-pyrazol-3-yl)amino]-2-bromo-3-oxopropyl}sulfanyl)methyl]-2-[(carboxymethyl)amino]-2-oxoethyl}glutamine;

10) N-5-{1-[({3-[(S-{[(5-{[(5-{[(2-amino(imino)methyl]amino}ethyl)amino]carbonyl}-1-methyl-1H-pyrrol-3-yl)amino]carbonyl-1-methyl-1H-pyrrol-3-yl)amino]carbonyl}-1-methyl-1H-pyrazol-3-yl)amino]-2-chloro-3-oxopropyl}sulfanyl)methyl]-2-[(carboxymethyl)amino]-2-oxoethyl}glutamine;

11) N-5-{1-[({3-[(2-{[(5-{[(5-{[(2-amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-imidazolyl)amino]-2-bromo-3-oxopropyl}sulfanyl)methyl]-2-[(carboxymethyl)amino]-2-oxoethyl}glutamine;

12) N-5-{1-[({3-[(2-{[(5- {[(5-{[(2-amino(imino)methyl]amino}ehtyl) amino]carbonyl}-1-methyl-1H-pyrrol-3-yl)amino]carbonyl}-1-methyl-1H-pyrrol-3-yl)amino]carbonyl}-1-methyl-1H-imidazol-4-yl)amino]-2-chloro-3-oxopropyl}sulfanyl)methyl]-2-[(carboxymethyl)amino]-2-oxoethyl}glutamine;

13) N-5-{1-[({3-[(5-{[(5-{[(5-{[5-(4-amino-4-iminobutanoyl)-1-methyl-1H-pyrrol-3-yl]amino]carbonyl)-1-methyl-1H-pyrrol-3-yl)amino]carbonyl)-1-methyl-1H-pyrrol-3-yl]amino}-carbonyl)-1-methyl-1H-pyrrol-3-yl]amino}-2-bromo-3-oxopropyl)sulfanyl]methyl]-2-[(carboxymethyl)amino]-2-oxoethyl}glutamine;

14) N-5-{1-[({3-[(S-{[(5-{[(5-{[(5-(4-amino-4-iminobutanoyl)-1-methyl-1H-pyrrol-3-yl]amino]carbonyl)-1-methyl-1H-pyrrol-3-yl]aminocarbonyl)-1-methyl-1H-pyrrol-3-yl]amino) carbonyl)-1-methyl-1H-pyrrol-3-yl]amino}-2-chloro-3-oxopropyl)sulfanyl]methyl]-2-[(carboxymethyl)amino]-2-oxoethyl}glutamine;

15) N-S-{1-[({3-[(5-{[(5-{[(5-{[5-(4-amino-4-iminobutanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-3-yl]amino)-2-bromo-3-oxopropyl)sulfanyl]methyl]-2-[(carboxymethyl)amino]-2-oxoethyl}glutamine;

16) N-5-{1-[({3-[(5-{[(5-{[(5-{[5-(4-amino-4-iminobutanoyl-1-methyl-1H-pyrrol-3-yl]amino}carbonyl)-1-methyl-1H-pyrrol-3-yl]amino)carbonyl)-1-methyl-1H-pyrrol-3-yl]amino) carbonyl)-1-methyl-1H-pyrazol-3-yl]amino}-2-chloro-3-oxopropyl)sulfanyl]methyl]-2-[(carboxymethyl)amino]-2-oxoethyl}glutamine;

17) N-5-{1-[({3-[(2-{[(5-{[(5-{[(5-(4-amino-4-iminobutanoyl-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-4-yl]amino)

-2-bromo-3-oxopropyl)sulfanyl]methyl}-2-[(carboxymethyl)amino]-2-oxoethyl}glutamine;
18) N-5-{1-[({3-[(2-{[(5-{[(5-{[5-(4-amino-4-iminobutanoyl-1methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-4-yl]amino}-2-chloro-3-oxopropyl)sulfanyl]methyl}-2-[(carboxymethyl)amino]-2-oxoethyl}glutamine;
19) N-5-{1-[({3-[(5-{[(5-{[(5-{[5-(3-{[amino(imino)methyl]amino}propanoyl)-1-methyl-1H-pyrrol-3-yl]amino}carbonyl)-1-methyl-1H-pyrrol-3-yl]amino)carbonyl)-1-methyl-1H-pyrrol-3-yl]amino}carbonyl)-1-methyl-1H-pyrrol-3-yl]amino) -2-bromo-3-oxopropyl}sulfanyl]methyl}-2-[(carboxymethyl)amino]-2-oxoethyl}glutamine;
20) N-S-{1-[({3-[(5-{[(5-{[(5-{[5-(3- {[amino(imino)methyl]amino}propanoyl)-1-methyl-1H-pyrrol-3-yl]amino) carbonyl)-1-methyl-1H-pyrrol-3-yl]amino}carbonyl)-1-methyl-1H-pyrrol-3-yl]amino}carbonyl)-1-methyl-1H-pyrrol-3-yl}amino)-2-chloro-3-oxopropyl}sulfanyl]methyl}-2-[(carboxymethyl)amino]-2-oxoethyl}glutamine;
21) N-5-{[-[({3-[(5-{[(5-{[(5-{[5-(3-{[amino(imino)methyl]amino}propanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-3-yl]amino}-2-bromo-3-oxopropyl)sulfanyl]methyl})-2-[(carboxymethyl)amino]-2-oxoethyl}glutamine;
22) N-5-1{1-[({3-(5-{[(5-{[(5-{[5-(3-{[amino(imino)methyl]amino}propanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-3-yl]amino}-2-chloro-3-oxopropyl}sulfanyl]methyl}-2-[(carboxymethyl)amino]-2-oxoethyl}glutamine;
23) N-5-{11-[({3-[(2-{[(5-{[(5-{[5-(3-{[amino(imino)methyl]amino}propanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-imidazol-4yl]amino)-2-bromo-3-oxopropyl}sulfanyl]methyl)-2-[(carboxymethyl)amino]-2-oxoethyl}glutamine;
24) N-5-{11-[({3-[(2-{[(5-{[(5-{[5-(3-{[amino(imino)methyl]amino}propanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-imidazolyl]amino}-2-chloro-3-oxopropyl}sulfanyl]methyl) -2-[(carboxymethyl)amino]-2-oxoethyl}glutamine.

A further object of the present invention is a process for the preparation of the compounds of formula (I), and the pharmaceutically acceptable salts thereof, comprising the reaction of glutathione with a compound of formula (V)

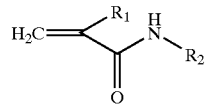

(V)

wherein $R_1$ and $R_2$ have the above described meanings; and the optional conversion of the compound of formula (1) thus obtained into a pharmaceutically acceptable salt thereof.

The preparation of the compounds of formula (I), according to the process object of the present invention, is performed by reacting the compounds of formula (V) with glutathione, preferably in excess, for instance with a molar ratio compound (V): glutathione ranging from about 1:1 to about 1:3, and in the presence of an organic or inorganic base such as, for instance, potassium carbonate, triethylamine or, preferably, sodium hydroxide.

The reaction may be performed in the presence of an organic solvent, for instance lower alcohols, dimethylsulfoxide or dimethylformamide, at a temperature comprised between About –101° C. to about 70° C. and for a period of time comprised between about 1 to about 6 hours. Preferably, the reaction is carried out in the presence of methanol or ethanol.

From the above it is clear to the skilled man that optional functional groups which could give rise to unwanted side products, hence interfering with the course of the reaction, may be conveniently protected according to well known methods. The amino and the carboxyl groups of glutathione, as an example, can be protected before performing the above reaction with the derivatives of formula (V) and afterwards deprotected, by operating according to known methods.

Likewise, the reaction of salification of the compounds of formula (I) can be performed according to conventional methods. Well known procedures such as, for instance, crystallization or chromatographic techniques, can be also employed for the separation of isomeric mixtures of the compounds of formula (I) into the single isomers.

Glutathione (The Merck Index XII Ed. N. 4483) and the acryloyl derivatives of distamycin of formula (V) are compounds known in the literature or may be obtained according to known methods, for instance as described in the aforementioned international patent applications WO 90/11277, WO 98/04524, WO 98/21202, WO 99/50265, WO 99/50266 and WO 01/40181.

Pharmacology

The compounds of formula (I), object of the present invention, exhibit cytotoxic properties and are thus useful, in therapy, in the treatment of various tumoral forms comprising, for instance, carcinoma of breast, lung, colon, ovary and endometrium, as well as other neoplasm including sarcoma or hematological malignant tumors, for instance leukemia The cytotoxic effect of the compounds of formula (I) was assessed in cells of human ovarian carcinoma (A2780). The cells have been maintained in-vitro as stabilized cultures, in culture medium RPMI 1640 added with bovine fetal serum (10%) and L-glutamine (2 mM). The cytotoxic effect has been evaluated in cells in exponential growth. The cells have been sown, 24 hours before treatment, on 96-well plates at the concentration of 5,000 cells/cm². Scalar doses of the compound to be tested have been added to the culture medium and the cells were incubated for one hour at 37° C. At the end of the treatment, the culture medium with the substances was removed and replaced with fresh culture medium. The cytotoxic effect of the compounds of formula (I) was evaluated after 72 hours by the MTT test (Cole S P. Rapid chemosensitivity testing of human lung tumor cells using the MTT assay; Cancer Chemotherapy & Pharmacology. 17(3):259–63, 1986). The antiproliferative effect of the compounds of formula (I) was calculated from the dose-response curves and expressed as the dose inhibiting the 50% of the cell growth in treated versus controls ($ID_{50}$).

The compounds of formula (I), tested under these experimental conditions, were found to be particularly active.

The compounds of formula (I) of the invention may be administered to mammals, including humans, according to conventional methods for example by parenteral route through intravenous injection or infusion, intramuscularly, subcutaneously or even by topical or oral route.

The exact dosage will depend from several factors among which are, as an example, the age, the body weight and the conditions of the patient to be treated, as well as from the selected method of administration.

A further object of the invention is represented by the pharmaceutical formulations which comprise the compounds of formula (I), as the active ingredient, and one or more pharmaceutically acceptable carriers or diluents. These pharmaceutical compositions are usually prepared according to conventional methods.

Object of the present invention is also a therapeutic method for the treatment of tumors comprising the administration of the compositions of the invention.

The compounds of formula (I) may be also administered in combination with other anti-neoplastic agents conventionally employed in therapy for the treatment of tumors.

Therefore, it is a further object of the present invention a combined preparation for the simultaneous, separate or sequential use, in anti-tumoral therapy, comprising a compound of formula (I) or a pharmaceutically acceptable salt thereof and an additional anti-tumoral agent.

Compounds with antitumoral activity which can be employed according to the object of the invention include, for instance, alkylating agents such as mustards, nitrosoureas, tetrazines, aziridines and platinum derivatives; inhibitors of topoisomerase I and II such as camptotecines and derivatives, anthracyclines and anthraquinone derivatives, acridine derivatives; taxanes or antimetabolites.

The following examples are here intended for a better understanding of the invention, but do not represent any limitation of it.

Example 1

N-5-{1-{[(3-{[5-({[5-({[-(3-{[amino(imino)methyl]amino}propanoyl)-1-methyl-1H-pyrrol-3-yl)amino}carbonyl)-1-methyl-1H-pyrrol-3-yl]amino}carbonyl}-1-methyl-1H-pyrrol-3-yl)amino{carbonyl)-1-methyl-1H-pyrrol-3-yl]amino}-chloro-3-oxopropyl)sulfanyl]methyl}-2-[(carboxymethyl)amino]-2-oxoethyl}glutamine (Compound 20).

A 2M (70 µl) sodium hydroxide solution was added to a suspension of glutathione (60 mg) in methanol (3 ml). The reaction mixture was stirred at room temperature for 2 hours and then added with 33 mg of N-[5-({[5-({[5-(3-{[amino(imino)methyl]amino}propanoyl)-1-methyl-1H-pyrrol-3-yl]amino}carbonyl)-methyl-1H-pyrrol-3-yl]amino}carbonyl)-1-methyl-1H-pyrrol-3-yl]-4-[(2-chloroacryloyl)amino]-1-methyl-1H-pyrrol-2-carboxamide, prepared as reported in WO 98/04524. After 2 hours the suspension was filtered, the precipitate was washed on the filter with a small amount of methanol and then dried in a stove at 40° C. under vacuum for 4 hours. 60 mg of the desired product were thus obtained, as a pale yellow solid.

FAB-MS: m/z 986, (100, [M+H]).

By operating in a similar way and by using the appropriate derivatives of formula (V), numerous other derivatives of formula (D) may be synthesized, such as the specific compounds from 1 to 19 and from 21 to 24, previously mentioned and numbered.

What is claimed is:

1. A distamycin derivative compound of formula (I)

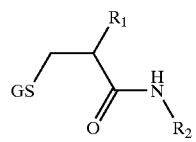

wherein:
R$_1$ is a bromine or chlorine atom;
R$_2$ is a distamycin;

GS represents a radical of formula (II)

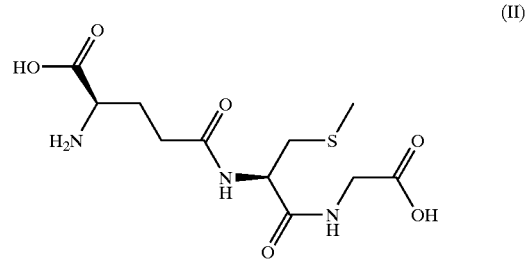

consisting of glutathione bound to the rest of the molecule through the sulfur atom; or a pharmaceutically acceptable salt thereof.

2. A compound of formula (I), according to claim 1, wherein R$_2$ is a group of formula (III):

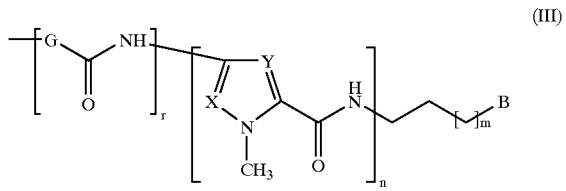

wherein:
m is 0, 1 or 2; n is an integer number from 2 to 5; r is 0 or 1;
X and Y are, independently for each heterocyclic ring, the same or different from each other and represent a nitrogen atom or a CH group;
G is phenylene or a saturated or unsaturated penta- or hexa-atomic heterocyclic ring with from 1 to 3 heteroatoms chosen among nitrogen, oxygen or sulfur, or G is a group of formula (IV)

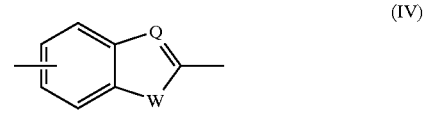

wherein Q is a nitrogen atom or a CH group and W is an oxygen or sulfur atom or it is a NR$_3$ group wherein R$_3$ is hydrogen or C$_1$–C$_4$-alkyl;
B is a group chosen among

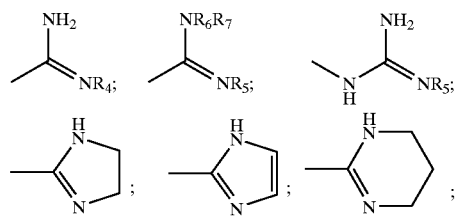

—CH ; —NR$_5$R$_6$; —CONR$_5$R$_6$; —NHCONR$_5$R$_6$
wherein R$_4$ is cyano, amino, hydroxy or C$_1$–C$_4$-alkoxy; R$_5$, R$_6$ and R$_7$, the same or different from each other, are hydrogen or C$_1$–C$_4$-alkyl.

3. A compound of formula (I), according to claim 2, where R$_1$ is bromine or chlorine; R$_2$ is a group of formula (III) where r is 0, m is 0 or 1, n is 4 and B as the above reported meanings.

4. A compound of formula (I), according to claim 3, where X and Y are both CH groups and B is chosen among:

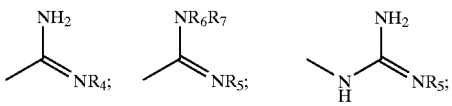

—CH; —CONR₅R₆; —NHCONR₅R₆ wherein R₄ is cyano or hydroxy and R₅, R₆ and R₇, the same or different from each other are hydrogen or C₁–C₄-alkyl.

5. A compound of formula (I), according to claim 4, where B is chosen between:

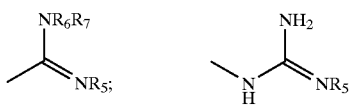

where R₅, R₆ and R₇ are hydrogen atoms.

6. A compound of formula (I), according to claim 1, optionally in the form of a pharmaceutically acceptable salt, chosen among:

1) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-chloro-3-oxopropyl}sulfanyl)methyl]-2-[(carboxymethyl)amino]-2-oxoethyl}glutamine, 2) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)amino]-2-bromo-3-oxopropyl}sulfanyl)methyl]-2-[(carboxymethyl)amino]-2-oxoethyl}glutamine;

3) N-5-{1-[({3-[(5-{[(5-{[(5-{[(3-amino-3-iminopropyl)amino]carbonyl}-1-methyl-1H-pyrrol-3-yl)amino]carbonyl}-2-chloro-3-oxopropyl}sulfanyl)methyl]-2-[(carboxymethyl)amino]-2-oxoethyl}glutamine;

4) N-5-{1-[({3-[(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrazol-3-yl)amino]-2-bromo-3-oxopropyl}sulfanyl)methyl]-2-[(carboxymethyl)amino]-2-oxoethyl}glutamine;

5) N-5-{1-[({3-[(2-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-imidazol-4-yl)amino]-2-chloro-3-oxopropyl}sulfanyl)methyl]-2-[(carboxymethyl)amino]-2-oxoethyl}glutamine;

6) N-5-{1-[({3-[(2-{[(5-{[(5-{[(3-amino-3-aminopropyl)amino]carbonyl}-1-methyl-1H-pyrrol-3-yl)amino]carbonyl}-1-methyl-1H-pyrrol-3-yl)amino]carbonyl}-1-methyl-1H-imidazol-4-yl)amino]-2-bromo-3-oxopropyl}sulfanyl)methyl]-2-[(carboxymethyl)amino]-2-oxoethyl}glutamine;

7) N-5-{1-[({3-[(5-{[(5-{[(5-{[(2-{[amino(imino)methyl]amino}ethyl) amino]carbonyl)-1-methyl-1H-pyrrol-3-yl)amino]carbonyl}-1-methyl-1-pyrrol-3-yl)amino]carbonyl}-1-methyl-1H-pyrrol-3-yl)amino]-2-bromo-3-oxopropyl}sulfanyl)methyl]-2-[(carboxymethyl)amino]-2-oxoethyl}glutamine;

8) N-5-{1-[({3-[(5-{[(5-{[(5-{[(2-amino(imino)methyl]amino}ethyl) amino]carbonyl)-1-methyl-1H-pyrrol-3-yl)amino]carbonyl}-1-methyl-1-pyrrol-3-yl)amino]carbonyl)-1-methyl-1H-pyrrol-3-yl)amino]-2-chloro-3-oxopropyl} sulfanyl)methyl]-2-[(carboxymethyl)amino]-2-oxoethyl}glutamine;

9) N-5-{1-[({3-[(5-{[(5-{[(5-{[(2-amino(imino)methyl]amino}ethyl) amino]carbonyl}-1-methyl-1H-pyrrol-3-yl)amino]carbonyl}-1-methyl-1-pyrrol-3-yl)amino]carbonyl}-1-methyl-1H-pyrazol-3-yl)amino]-2-bromo-3-oxopropyl) sulfanyl)methyl]-2-[(carboxymethyl)amino]-2-oxoethyl}glutamine;

10) N-5-{1-[({3-[(5-{[(5-{[(5-{[(2-amino(imino)methyl]amino}ethyl) amino]carbonyl}-1-methyl-1H-pyrrol-3-yl)amino]carbonyl}-1-methyl-1-pyrrol-3-yl)amino]carbonyl}-1-methyl-1H-pyrazol-3-yl)amino]-2-chloro-3-oxopropyl) sulfanyl)methyl]-2-[(carboxymethyl)amino]-2-oxoethyl) glutamine;

11) N-5-{1-[({3-[(2-{[(5-{[(5-{[(2-amino(imino)methyl]amino}ethyl) amino]carbonyl}-1-methyl-1H-pyrrol-3-yl)amino]carbonyl}-1-methyl-1-pyrrol-3-yl)amino]carbonyl}-1-methyl-1H-imidazol-4-yl)amino]-2-bromo-3-oxopropyl) sulfanyl)methyl]-2-[(carboxymethyl)amino]-2-oxoethyl}glutamine;

12) N-5-{1-[({3-[(2-{[(5-{[(5-{[(2-amino(imino)methyl]amino}ethyl) amino]carbonyl}-1-methyl-1H-pyrrol-3-yl)amino]carbonyl}-1-methyl-1-pyrrol-3-yl)amino]carbonyl}-1-methyl-1H-imidazol-4-yl)amino]-2-chloro-3-oxopropyl) sulfanyl)methyl]-2-[(carboxymethyl)amino]-2-oxoethyl}glutamine;

13) N-5-{1-[({3-[(5-{[(5-{[(5-{[(5-(4-amino-4-iminobutanoyl)-1-methyl-1H-pyrrol-3-yl]amino]carbonyl)-1-methyl-1H-pyrrol-3-yl)amino]carbonyl)-1-methyl-1H-pyrrol-3-yl]amino}-carbonyl)-1-methyl-1H-pyrrol-3-yl]amino}-2-bromo-3-oxopropyl) sulfanyl]methyl]-2-[(carboxymethyl)amino]-2-oxoethyl}glutamine;

14) N-5-{1-[({3-[(5-{[(5-{[(5-{[(5-(4-amino-4-iminobutanoyl)-1-methyl-1H-pyrrol-3-yl)amino]carbonyl)-1-methyl-1H-pyrrol-3-yl]amino}carbonyl)-1-methyl-1H-pyrrol-3-yl]amino}carbonyl)-1-methyl-1H-pyrrol-3-yl]amino}-2-chloro-3-oxopropyl) sulfanyl]methyl}-2-[(carboxymethyl)amino]-2-oxoethyl}glutamine;

15) N-5-{1-[({3-[(5-{[(5-{[(5-{[(5-(4-amino-4-iminobutanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-3-yl]amino}-2-bromo-3-oxopropyl)sulfanyl]methyl]-2-carboxymethyl]amino]-2-oxoethyl}glutamine;

16) N-5-{1-[({3-[(5-{[(5-{[(5-{[(5-(4-amino-4-iminobutanoyl)-1-methyl-1H-pyrrol-3-yl]amino}carbonyl)-1-methyl-1H-pyrrol-3-yl]amino}carbonyl)1-methyl-1H-pyrrol-3-yl]amino}carbonyl)-1-methyl-1H-pyrazol-3-yl]amino}-2-chloro-3-oxopropyl}sulfanyl]methyl}-2-[(carboxymethyl)amino]-2-oxoethyl}glutamine;

17) N-5-{1-[({3-[(2-{[(5-{[(5-{[(5-(4-amino-4-iminobutanoyl)-1-methyl-1H-pyrrol-3-yl]amino}carbonyl)-1-methyl-1H-pyrrol-3-yl]amino}carbonyl)-1-methyl-1H-pyrrol-3-yl]amino}carbonyl)-1-methyl-1H-pyrazol-4-yl]amino}-2-bromo-3-oxopropyl)sulfanyl]methyl]-2-[(carboxymethyl)amino]-2-oxoethyl}glutamine;

18) N-5-{1-[({3-[(2-{[(5-{[(5-{[(5-(4-amino-4-iminobutanoyl)-1-methyl-1H-pyrrol-3-yl]amino}carbonyl)-1-methyl-1H-pyrrol-3-yl]

amino}carbonyl)-1-methyl-1H-pyrrol-3-yl]amino}carbonyl)-1-methyl-1H-pyrazol-4-yl]amino)-2-chloro-3-oxopropyl)sulfanyl]methyl}-2-[(carboxymethyl)amino]-2-oxoethyl} glutamine;

19) N-5-{1-[({3-[(5-{[(5-{[(5-(3-{[amino(imino) methyl]amino}propanoyl)-1-methyl-1H-pyrrol-3-yl] amino) carbonyl)-1-methyl-1H-pyrrol-3-yl] amino}carbonyl)-1-methyl-1H-pyrrol-3-yl] amino}carbonyl)-1-methyl-1H-pyrrol-3-yl]amino}-2-bromo-3-oxopropyl) sulfanyl]methyl)-2-[(carboxymethyl)amino]-2-oxoethyl} glutamine;

20) N-5-{1-[({3-[(5-{[(5-{[(5-(3-{[amino(imino) methyl]amino}propanoyl)-1-methyl-1H-pyrrol-3-yl] amino}carbonyl)-1-methyl-1H-pyrrol-3-yl] amino}carbonyl)-1-methyl-1H-pyrrol-3-yl] amino}carbonyl)-1-methyl-1H-pyrrol-3-yl]amino}-2-chloro-3-oxopropyl}sulfanyl]methyl}-2-[(carboxymethyl)amino]-2-oxoethyl}glutamine;

21) N-5-{1-[({3-[(5-{[(5-{[(5-{[(5-(3-{[amino(imino) methyl]amino}propanoyl-1-methyl-1H-pyrrol-3-yl] amino}carbonyl)-1-methyl-1H-pyrrol-3-yl]amino} carbonyl)-1-methyl-1H-pyrrol-3-yl]amino}carbonyl)-1-methyl-1H-pyrazol-3-yl]amino}-2-bromo-3-oxopropyl)sulfanyl]methyl}-2-[(carboxymethyl) amino]-2-oxoethyl}glutamine;

22) N-5-{1-[({3-[(5-{[(5-{[(5-{[(5-(3-{[amino(imino) methyl]amino}propanoyl)-1-methyl-1H-pyrrol-3-yl] amino}carbonyl)-1-methyl-1H-pyrrol-3-yl] amino}carbonyl)-1-methyl-1H-pyrrol-3-yl] amino}carbonyl)-1-methyl-1H-pyrazol-3-yl]amino}-2-chloro-3-oxopropyl}sulfanyl]methyl}-2-[(carboxymethyl)amino]-2-oxoethyl}glutamine;

23) N-5-{1-[({3-[(2-{[(5-{[(5-{[(5-(3-{[amino(imino) methyl]amino}propanoyl)-1-methyl-1H-pyrrol-3-yl] amino}carbonyl)-1-methyl-1H-pyrrol-3-yl] amino}carbonyl)-1-methyl-1H-pyrrol-3-yl] amino}carbonyl)-1-methyl-1H-imidazol-4-yl]amino}-2-bromo-3-oxopropyl}sulfanyl]methyl}-2-[(carboxymethyl)amino]-2-oxoethyl}glutamine;

24) N-5-{1-[({3-[(2-{[(5-{[(5-{[(5-(3-{[amino(imino) methyl]amino}propanoyl)-1-methyl-1H-pyrrol-3-yl] amino}carbonyl)-1-methyl-1H-pyrrol-3-yl] amino}carbonyl)-1-methyl-1H-pyrrol-3-yl] amino}carbonyl)-1-methyl-1H-imidazol-4-yl]amino)-2-chloro-3-oxopropyl}sulfanyl]methyl}-2-[(carboxymethyl)amino]-2-oxoethyl}glutamine.

7. A process for the preparation of the compound of formula (I), as defined in claim 1, and pharmaceutically acceptable salts thereof, comprising the reaction of glutathione with a compound of formula (V)

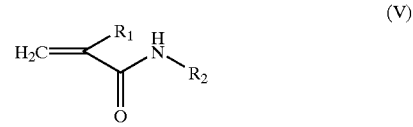

(V)

where $R_1$ and $R_2$ have the meanings as from claim 1; and the optional conversion of the compound of formula (I) thus obtained into its pharmaceutically acceptable salt.

8. A process according to claim 7 wherein the reaction is carried out with an excess of glutathione and in the presence of an organic or inorganic base.

9. A process according to claim 8 wherein the molar ratio between the compound of formula (V) and glutathione ranges from about 1 to 1 to about 1 to 3.

10. A pharmaceutical formulation comprising a therapeutically effective amount of a compound of formula (I) as from claim 1, as active ingredient, and one or more pharmaceutically acceptable carriers or diluents.

11. A therapeutic method for the treatment of tumors comprising the administration to a patient in need thereof the pharmaceutical formulation according to claim 10.

12. A combined preparation for the simultaneous, separate or sequential use in antitumor therapy, comprising a compound of formula (I), according to claim 1 or its pharmaceutically acceptable salt, and an additional antitumor agent.

13. A method for inhibiting tumor activity in a mammal in need thereof comprising administering the compound of formula (I), as defined in claim 1 to said mammal.

* * * * *